US009532941B2

(12) United States Patent
Shapiro et al.

(10) Patent No.: US 9,532,941 B2
(45) Date of Patent: *Jan. 3, 2017

(54) METHOD FOR TREATMENT OF HAIR LOSS WITH A COMBINATION OF NATURAL INGREDIENTS

(71) Applicant: Pilaris Labs LLC, Palm Beach Gardens, FL (US)

(72) Inventors: Steven D. Shapiro, Palm Beach Gardens, FL (US); Michael T. Borenstein, Palm Beach Gardens, FL (US)

(73) Assignee: Pilaris Labs LLC, Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/659,707

(22) Filed: Mar. 17, 2015

(65) Prior Publication Data
US 2015/0265528 A1 Sep. 24, 2015

Related U.S. Application Data

(63) Continuation of application No. 13/369,711, filed on Feb. 9, 2012, now Pat. No. 8,985,124.

(60) Provisional application No. 61/441,063, filed on Feb. 9, 2011, provisional application No. 61/496,071, filed on Jun. 13, 2011.

(51) Int. Cl.
| | | |
|---|---|---|
| A61K 8/97 | (2006.01) | |
| A61K 8/49 | (2006.01) | |
| A61Q 5/02 | (2006.01) | |
| A61Q 5/12 | (2006.01) | |
| A61Q 7/00 | (2006.01) | |
| A61K 31/353 | (2006.01) | |
| A61K 31/522 | (2006.01) | |
| A61K 36/889 | (2006.01) | |

(52) U.S. Cl.
CPC ............... *A61K 8/97* (2013.01); *A61K 8/498* (2013.01); *A61K 8/4953* (2013.01); *A61K 31/353* (2013.01); *A61K 31/522* (2013.01); *A61K 36/889* (2013.01); *A61Q 5/02* (2013.01); *A61Q 5/12* (2013.01); *A61Q 7/00* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 4,833,147 A | 5/1989 | Moeller | |
| 5,972,345 A | 10/1999 | Chizick | |
| 6,193,976 B1 | 2/2001 | Porras | |
| 6,207,694 B1 | 3/2001 | Murad | |
| 6,358,541 B1 | 3/2002 | Goodman | |
| 6,878,145 B2 | 4/2005 | Brugger | |
| 7,713,557 B2 | 5/2010 | Choi | |
| 8,080,524 B2 | 12/2011 | Bakala | |
| 8,985,124 B2 | 3/2015 | Shapiro et al. | |
| 2002/0034485 A1 | 3/2002 | Noser | |
| 2004/0096420 A1 | 5/2004 | Catalfo | |
| 2004/0171693 A1 | 9/2004 | Gan et al. | |
| 2006/0039878 A1 | 2/2006 | Khoshdel | |
| 2007/0077222 A1 | 4/2007 | Shapiro et al. | |
| 2007/0141019 A1 | 6/2007 | Long | |
| 2012/0199152 A1 | 8/2012 | Shapiro et al. | |

OTHER PUBLICATIONS

F. Alan Andersen. Final Report on the Safety Assessment of Cocamide MEA. International Journal of Toxicology Mar. 1999 18: 9-16, doi:10.1177/109158189901800204.*
Rossi A, et al., Int J lmmunopathol Pharmacol. Comparitive effectiveness of finasteride vs Serenoa repens in male androgenetic alopecia: a two-year study, Oct.-Dec. 2012:25(4):1167-73. (Abstract).
Stahl J, Niedorf F, et al., The in vitro use of the hair follicle closure technique to study the follicular and percutaneous permeation of topically applied drugs., Altern Lab Anim. Mar. 2012;40(1):51-7. (Abstract).
Otberg N, et al., Skin Pharmacol Physiol. Follicular penetration of topically applied caffeine via a shampoo formulation, 2007;20(4):195-8. Epub Mar. 29, 2007 (Abstract).
Kim YY., et al., Effects of topical application of EGCG on testosterone-induced hair loss in a mouse model. Dec. 2011;20(12):1015-7. doi: 10.1111/j.1600-0625.2011.01353.x. Epub Sep. 22, 2011 (Abstract).
Otberg N, et al., The role of hair follicles in the percutaneous absorption of caffeine. Br J Clin Pharmacol. 2007;65:488-92. (Abstract).
Otberg N.,et al., Follicular penetration of topically applied caffeine via a shampoo formulation. Skin Pharmacol Physiol. 2007;20:195-8.
Pilarismax, PilarisMax Shampoo, Triple Action Hair Care Aid for Men, website- www.pilarismax.com, Pilaris Laboratories, p. 1, Copyright 2011.
Fischer TW, et al., (Abstract)—"Effect of Caffeine and Testosterone on the Proliferation of Human Hair Follicles In Vitro",Department of Dermatology, Int J Dermatol. 46(1):27-35 2007.
Hsu S., (Abstract)—"Green Tea and the Skin" Journal of the American Academy of Dermatology Jun. 2005;52 (6):1049-1059.
Wong, Cathy; "Can Saw Palmetto Stop Hair Loss?" —About.com website under "Alternative Medicine"; pp. 2, accessed on Jan. 31, 2012.

(Continued)

*Primary Examiner* — Ileana Popa
*Assistant Examiner* — Nicole Babson
(74) *Attorney, Agent, or Firm* — Fleit Gibbons Gutman Bongini & Bianco PL; Paul D. Bianco; Katharine Wong Davis

(57) ABSTRACT

The invention provides a composition for topical treatment of hair loss/alopecia including three natural, active ingredients, caffeine, saw palmetto berry extract, and epigallocatechin-3-gallate (EGCG). The invention also provides methods for using this composition to treat hair loss.

6 Claims, No Drawings

(56) References Cited

OTHER PUBLICATIONS

Esfandiari A., et al. "The Effects of Tea Polyphenolic Compounds on Hair Loss among Rodents" Journal of the National Medical Association 97(8):1165-1169 2005).
Kwon OS, et al., (Abstract)—Human Hair Growth Enhancement In Vitro by Green Tea Epigallocatechin-3-Gallate (EGCG), Phytomedicine Aug. 2007;14:551-555.
Hiipakka RA, et al. (Abstract)—"Structure-activity Relationships for inhibition of Human 5alpha-reductases by Polyphenois"—Biochemical Pharmacology Mar. 15, 2002;63(6):1165-1176.

* cited by examiner

METHOD FOR TREATMENT OF HAIR LOSS WITH A COMBINATION OF NATURAL INGREDIENTS

CROSS REFERENCE TO RELATED APPLICATIONS

This application is a continuation application of U.S. patent application Ser. No. 13/369,711, filed on Feb. 9, 2012, which claimed the benefit of priority to U.S. Provisional Patent Application No. 61/441,063, filed on Feb. 9, 2011, and to U.S. Provisional Patent Application No. 61/496,071, filed on Jun. 13, 2011, the contents of each of the above-identified patent applications are hereby incorporated by reference in their entirety.

This application is related to U.S. Utility Patent Application No. 11/242,207, filed on Oct. 3, 2005, now abandoned, the content of which is hereby incorporated by reference in its entirety.

The foregoing applications and all documents cited therein or during their prosecution, and all documents cited or referenced herein, together with any manufacturer's instructions, descriptions, product descriptions, and product sheets for any product mentioned herein or in any document incorporated by reference herein, are all hereby incorporated herein by reference, and may be used in the practice of the invention.

FEDERAL SPONSORSHIP

This work was not federally sponsored research or development.

FIELD OF THE INVENTION

The invention generally relates to compositions and methods for treating hair loss, particularly to compositions for treating hair loss by reducing the effects of 5α-dihydrotestosterone (DHT), and most particularly to compositions for treating hair loss including three natural, active ingredients, caffeine, saw palmetto berry extract/derivative, and epigallocatechin-3-gallate (EGCG).

BACKGROUND

Millions of Americans experience some degree of alopecia, commonly referred to as "balding" or simply "hair loss", resulting in ever-increasing amounts of money being spent in efforts to stop the loss and/or grow the hair back.

Countless pharmaceutical remedies, cosmetic treatments, and surgical methods of varying success have been devised in order to address the problem of hair loss. The difficulty in identifying effective treatments stems from the fact that there is no one cause for hair loss, but rather, there are many, such as: hormonal changes, heredity, disease, stress, medications, infections, genetic disorders, toxic agents, and/or food deficiencies.

The majority of cases are hormonal in origin, for example—androgenic alopecia (also known as male-pattern alopecia and androgenetic alopecia), which is a distressing problem for a large proportion of adult men. This male balding most often starts between the ages of 30-50 years old. Occasionally, it may begin at an even younger age.

In men developing androgenic alopecia, there is a gradual atrophy of hair follicles due to a genetically-inherited sensitivity to 5α-dihydrotestosterone (also know as "dihydrotestosterone" or "DHT"). The enzyme 5-α-reductase transforms testosterone into dihydrotestosterone in the hair follicles, which then directs follicles to progressively shrink and finally disappear. Thus, considering that 5α-dihydrotestosterone is a key contributing factor to the onset and progression of androgenic alopecia, blocking DHT is an area of interest for protecting hair.

Although there are currently many accepted oral and topical treatments for balding, only two drugs have been approved by the Food and Drug Administration (FDA) to treat alopecia; topical minoxidil (trademark name-Rogaine®) and oral finasteride (trademark name-Propecia®).

Minoxidil, (trademark name-Rogaine®), was originally developed as a treatment for individuals with high blood pressure. While treating these individuals, it was discovered that minoxidil moderately increased hair growth and prevented future hair loss. It is also believed that minoxidil may increase hair growth in thinning hair areas, but the mechanism of action (of minoxidil) remains unknown.

However, although these advantages of use exist, there are problems associated with the use of minoxidil. The most common side effect of topical minoxidil is skin irritation and/or a local allergic reaction called contact dermatitis. Additionally, if the medication is stopped after prolonged use, hair loss may actually increase rather than decrease. Further, major complications of minoxidil are rare, but possible, and can include decreased blood pressure with headache, fatigue, and dizziness. Patients who suffer from heart disease or hypertension cannot utilize minoxidil without medical supervision.

Minoxidil in lower concentration is a non-prescription product currently sold over-the-counter in multiple different formulations for treatment of hair loss in both men and women.

The second FDA-approved drug is finasteride (trademark name-Propecia®). Finasteride was originally used to treat prostate enlargement by inhibiting the 5-α reductase enzyme. The inhibition of the 5-α reductase enzyme interferes with the formation of DHT by blocking the action of 5-α reductase on testosterone. Men undergoing this treatment experienced an increase in hair growth. It is believed that the inhibition of the 5-α reductase enzyme may increase hair follicle growth or prevent future hair follicle loss.

However, although these advantages of use exist, there are also problems associated with the use of finasteride. Men may experience decreased libido, decreased volume of ejaculate, and a lowered level of prostate specific antigen (PSA). This lowered level of PSA may interfere with screening for prostate cancer.

Further, pregnant or nursing women may not use finasteride because it is teratogenic, and can harm the human fetus. Due to such a serious health risk, finasteride has been limited to use within male patient populations only, leaving a majority of female alopecia sufferers to seek alternative treatment options.

A topical treatment for androgenic alopecia will have lower internal exposure leading to a lower internal side effect profile than oral medications such as finasteride. Currently available topical medications, i.e. minoxidil, have not worked consistently or effectively for balding. In theory, topical medications targeted at interfering with the production of testosterone derivatives or blocking the effects of dihydrotestosterone on its receptor (stopping the trigger of male-pattern hair loss) would be beneficial, but to date, none have been satisfactorily successful.

For additional background information regarding hair loss/alopecia, see U.S. Pat. Nos. 6,878,145 B2; 7,713,557 B2; and 8,080,524 B2.

Citation or identification of any reference/document in the instant application is not and should not be interpreted as an admission that such reference/documents is available as prior art to the present invention.

SUMMARY OF THE INVENTION

The invention provides a topical composition for improving treatments for human hair loss (alopecia) by reducing the effects of 5α-dihydrotestosterone (DHT) and thus, enhancing hair loss prevention and/or hair growth promotion.

The terms "hair loss", "alopecia", "balding", and "pattern hair loss" are used interchangeably herein.

A "topical composition" or "topical formulation" refers to a product that is applied externally to a part of the body and/or is applied only on the surface. Thus, topical treatments limit exposure to a local area and avoid systemic exposure.

The composition includes three natural, active ingredients, caffeine, saw palmetto berry extract/derivative, and epigallocatechin-3-gallate (EGCG) which work directly at the site of the pathway, i.e. conversion of testosterone to dihydroxytestosterone by 5-α-reductase, for pattern alopecia.

In one embodiment of the invention, the composition is a liquid in the form of a shampoo, a conditioner, a tonic, a combination shampoo/conditioner, or a combination shampoo/conditioner/tonic.

Shampoo, as used herein, refers to compositions that are known in the art as shampoos. A shampoo is a composition that is applied to the scalp or hair for the general purpose of cleaning the scalp and/or hair. Shampoos may include various components known in the art, for example, but not limited to, soap, cleansers, detergents (sodium lauryl sulfate), surfactants, fragrances, anti-dandruff agents, thickening agents, humectants, moisturizers, glycol, polysorbate, and/or citric acid.

Conditioner, as used herein, refers to compositions that are known in the art as conditioners. A conditioner is a composition that is applied to the scalp or hair for the general purpose of conditioning the scalp or hair, for example, but not limited to, improving texture or tone, de-tangling, lubricating, softening, moisturizing, thickening, and/or improving shine. Conditioners may include various components known in the art, for example, but not limited to, glossers (silicone compounds), polyalkylene glycol, reconstructors, thermal protectors, lubricants (panthenol), acidifiers, oils, preservatives, and/or anti-static agents. Conditioners can be the rinse-off type or the leave-in (not rinsed off) type.

Tonic, as used herein, refers to a solution, liquid, foam, or gel applied to the scalp to improve hair without providing the benefits of a shampoo and/or conditioner.

As used herein, the combination shampoo/conditioner or the combination shampoo/conditioner/tonic refers to compositions that combine the characteristics of a shampoo and conditioner or the characteristics of a shampoo, conditioner, and tonic, respectively.

In another embodiment of the invention, the composition is a dermatological composition associated with the integumentary system, i.e. skin, hair, and/or nails.

In another embodiment of the invention, the composition is a cosmeceutical composition that is available to the public over-the-counter (without the requirement of a prescription) and used to improve the integumentary system.

In one embodiment, the invention provides a topical hair treatment in which the treatment is a liquid in the form of a shampoo, a conditioner, a tonic, a combination shampoo/conditioner, or a combination shampoo/conditioner/tonic and includes approximately 0.01 to 0.19 mg/ml of caffeine (0.001% to 0.19% weight of caffeine/final volume).

As used herein, 1% weight=1000 mg per 100 ml final volume.

The caffeine included in the composition can be hydrous caffeine, caffeine salts, or complexes breaking down to yield caffeine.

In accordance with another feature of the invention, the caffeine is included in the liquid composition in an amount of approximately 0.1 mg/ml (0.01% weight of caffeine/per final volume).

In another embodiment, the invention provides a topical hair treatment in which the treatment is a liquid in the form of a shampoo, a conditioner, a tonic, a combination shampoo/conditioner, or a combination shampoo/conditioner/tonic and includes approximately 0.01 mg/ml to 0.2 mg/ml of a saw palmetto berry derivative (0.001% to 0.02% weight of saw palmetto berry derivative/final volume).

The saw palmetto berry derivative included in the composition can be a saw palmetto berry extract or a hydrous saw palmetto berry extract.

In accordance with another feature of the invention, the saw palmetto berry derivative is included in the liquid composition in an amount of approximately 0.1 mg/ml (0.01% weight of saw palmetto berry derivative/per final volume).

In another embodiment, the invention provides a topical hair treatment in which the treatment is a liquid in the form of a shampoo, a conditioner, a tonic, a combination shampoo/conditioner, or a combination shampoo/conditioner/tonic and includes approximately 0.5 mg/ml to 50 mg/ml of an epigallocatechin-3-gallate (EGCG) derivative (0.05% to 5% weight of EGCG/final volume).

The epigallocatechin-3-gallate (EGCG) derivative included in the composition can be an extract powder, an extract liquid, or a lyophilized power extracted using water and pure grain alcohol.

In accordance with another feature of the invention, the epigallocatechin-3-gallate (EGCG) derivative is included in the liquid composition in an amount of approximately 2.5 ml/mg (0.25% weight of EGCG/per final volume).

In yet another embodiment, the invention provides a topical hair treatment in which the treatment is a liquid in the form of a shampoo, a conditioner, a tonic, a combination shampoo/conditioner, or a combination shampoo/conditioner/tonic and includes approximately 0.01 to 0.19 mg/ml of caffeine (0.001% to 0.19% weight of caffeine/final volume); approximately 0.01mg/ml to 0.2 mg/ml of a saw palmetto berry derivative (0.001% to 0.02% weight of saw palmetto berry derivative/final volume; and approximately 0.5 mg/ml to 50 mg/ml of an epigallocatechin-3-gallate (EGCG) derivative (0.05% to 5% weight of EGCG/final volume).

The instant invention also provides a method for treating hair loss in a human subject undergoing treatment for hair loss. The steps of the method include preparing any of the topical compositions described herein; moistening the scalp and/or hair of the subject; blending the composition; applying the composition to the moistened scalp and/or hair; massaging the composition into the scalp and/or hair (for example, by using a circular motion); leaving the composition on the scalp and/or hair for a period of time; and rinsing the composition from the scalp and/or hair.

As used herein, the terms "treat" and "treating" refer to the reduction, slowing, stopping, limiting, and/or elimination of hair loss (alopecia). The treatment may also improve hair quality and texture so as to minimize effects of hair loss (alopecia) on appearance.

As used herein, a "subject" or "person" is any human being experiencing hair loss and/or any human being in need of treatment for such hair loss.

In addition to human beings, animals can also suffer from a variety of dermatologic conditions causing and/or resulting in hair loss. Thus, the term "subject" also encompasses animals.

When carrying out the method, the composition may be left on the scalp and/or in the hair for any period of time deemed necessary. However, the preferred range is a time period of at least two to five minutes.

The method may be carried out on a daily basis, every day, weekly, or any other time intervals deemed to be effective in providing the desired improvements.

The method encompasses applying a shampoo, a conditioner, a tonic, a combination shampoo/conditioner, and a combination shampoo/conditioner/tonic. Any of these may be "leave-in" meaning that they are combed or brushed throughout areas of the scalp and/or hair and are left on the scalp and/or hair and not rinsed out.

Accordingly, it is therefore an objective of the invention to provide compositions and methods for treating hair loss (alopecia, balding).

It is an objective of the invention to provide compositions for topical application to the scalp and/or hair.

It is another objective of the invention to provide a product for balding and/or hair loss that does not require a prescription for distribution or use, i.e. the product is over-the-counter.

It is yet another objective of the invention to provide a composition that improves hair quality and texture so as to minimize effects of hair loss (alopecia) on appearance.

It is another objective of the invention to provide compositions for treating hair loss by reducing the effects of 5α-dihydrotestosterone (DHT).

It is another objective of the invention to provide compositions for treating hair loss including three natural, active ingredients, caffeine, saw palmetto berry extract/derivative, and epigallocatechin-3-gallate (EGCG).

It is yet another objective of the invention to provide a formulation of DHT blockers in solution having beneficial effects in hair loss patients.

It is still another objective of the invention to provide a composition for topical application to a human scalp including about 0.01 to about 0.19 mg/ml of caffeine, which is about 0.001% to about 0.019% weight of caffeine/final volume; about 0.01 to about 0.2 mg/ml of a saw palmetto berry derivative, which is about 0.001% to about 0.02% weight of saw palmetto berry derivative/final volume; and about 0.5 to about 50 mg/ml of an epigallocatechin-3-gallate (EGCG) derivative, which is about 0.05% to about 5% weight of EGCG/final volume.

It is another objective of the invention to provide a method for treatment of hair loss including the steps of preparing any of the topical compositions described herein; moistening the scalp and/or hair of the subject; blending the composition; applying the composition to the moistened scalp and/or hair; massaging the composition into the scalp and/or hair (for example, by using a circular motion); leaving the composition on the scalp and/or hair for a period of time; and rinsing the composition from the scalp and/or hair.

Although the invention is described herein as embodied in a combination of natural products (caffeine, saw palmetto berry derivative, and epigallocatechin-3-gallate (EGCG) derivative) for hair loss patients, it is, nevertheless, not intended to be limited to the details described because various modifications and structural changes may be made therein without departing from the spirit of the invention.

Thus, the above embodiments, features, and objectives are merely exemplary of the invention. Other objectives and advantages of this invention will become apparent from the following description of specific formulations.

DETAILED DESCRIPTION OF THE INVENTION

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described compositions, methods, products, kits, and/or any further application of the principles of the invention as described herein, are contemplated as would normally occur to one skilled in the art to which the invention relates.

The instant invention provides a topical, natural, and safe composition (and methods of use thereof) that will improve hair loss treatment, including treatment in men (androgenic alopecia) and treatment in post-menopausal women (female-pattern hair loss).

A relationship between testosterone levels and hair loss has been well-described in the pathogenesis of this distressing condition. Blockers of testosterone and its metabolite, 5α-dihydrotestosterone (DHT), have been used systematically to treat male-pattern hair loss.

Caffeine, saw palmetto berry extract, and epigallocatechin-3-gallate (EGCG) have found to have varying effects on 5α-dihydrotestosterone through different mechanisms.

Fischer (Fischer et al. *Int J Dermatol.* 46(1):27-35 2007) demonstrated the effect of caffeine and testosterone on the proliferation of human hair follicles in vitro. Significant growth suppression was found in hair follicles treated with 5 mg/ml testosterone. This suppression was counteracted by caffeine in concentrations of 0.001% and 0.005%. Additionally, caffeine alone led to significant stimulation of hair follicle growth.

In medical literature to date, these observations have not been reported with topical preparations of caffeine in vivo.

Topical preparations using caffeine in high concentrations of about 1% of weight per unit volume or greater has a vasoconstrictive effect. Vasoconstriction is understood to decrease blood flow to the hair follicles, and thereby, inhibit hair growth. Thus, using caffeine for hair loss prevention in vivo is not found in the art. The present invention uses a concentration of caffeine (about 0.01 to about 0.19 mg/ml of caffeine, which is about 0.001% to about 0.019% weight of caffeine/final volume) that avoids vasoconstriction, but maintains its reducing effects on 5α-dihydrotestosterone (DHT).

Saw palmetto (*Serenoa repens* or *Sabal serrulata*) is a dwarf palm plant native to North America growing primarily along the southern Atlantic coast of the United States. An extract has been derived from the berries of this palm plant (saw palmetto berry extract) which has been used orally for its effects on testosterone and dihydrotestosterone in prostate disease such as benign prostate gland enlargement (benign prostatic hyperplasia, BPH). Although it has not been scientifically confirmed, it is believed that saw palmetto berry extract may block the 5-α-reductase enzyme from converting testosterone into dihydroxytestosterone. See "Can Saw Palmetto Stop Hair Loss?" by Cathy Wong at the About.com website under "Alternative Medicine"; accessed on Jan. 31, 2012.

Considering that saw palmetto berry extract has been used orally for its effects on testosterone and dihydroxytestosterone in the treatment of prostate disease, it is a potentially-beneficial treatment for alopecia (hair loss). Saw palmetto berry extract can be used in combination with a low concentration of caffeine to reduce the effects of dihydroxytestosterone and thereby, treat alopecia (hair loss).

Epigallocatechin-3-gallate (EGCG) is a natural polyphenolic compound found in green tea. It has been reported that EGCG may be useful for selectively inhibiting 5-α-reductase activity and several studies have demonstrated its effects on hair growth.

Hiipakka (Hiipakka et al. *Biochemical Pharmacology* 63(6):1165-1176 2002) showed that epigallocatechin-3-gallate (EGCG) potently inhibited human 5-α-reductase in cell free but not in whole cell assays in vitro.

Kwon (Kwon et al. Phytomedicine 14:551-555 2007) showed that in vitro exposure of human hair to topical EGCG demonstrated changes that were consistent with in vivo changes for cell proliferation markers in pathways known to participate in growth. Thus, Kwon suggested that EGCG stimulates human hair growth. Kwon's formula contained EGCG in 10% ethanol which was used in human volunteers. This formulation is not useful for repeated topical application due to the irritant and other side effects of the 10% ethanol.

Esfandiari (Esfandiari et al. *Journal of the National Medical Association* 97(8):1165-1169 2005) showed, using a mouse model for hair loss, that mice given green tea in their drinking water had a 33% hair re-growth rate compared to mice receiving unsupplemented drinking water.

Green tea extracts have not been widely considered as effective for topical delivery as the extracts rapidly degrade in aqueous solution and are unlikely to penetrate an intact epidermal barrier. Hsu, S. *Journal of the American Academy of Dermatology* 52(6):1049-1059 2005. Additionally, even high topical concentrations failed to deliver significant levels in preliminary studies.

Thus, although caffeine, saw palmetto berry extract, and epigallocatechin-3-gallate (EGCG) have been shown to have similar effects, they have never been used together prior to the instant invention. There are no published reports in the scientific literature that demonstrate direct effects of topical EGCG in humans undergoing hair loss therapy. Additionally, there are no published reports in the medical literature that topical formulation of caffeine changed levels of testosterone or dihydroxytestosterone to suggest that topical treatment might have an effect on hair loss. Further, saw palmetto berry extract has not been shown to have effects in topical formulations.

Accordingly, no studies or reports have been shown to use these three compounds (caffeine, saw palmetto berry extract, and EGCG) simultaneously to reduce the effects of dihydroxytestosterone (DHT) on the complex DHT receptor expressed on hair follicles, which effects trigger female and male-pattern hair loss. Further, these three compounds (caffeine, saw palmetto berry extract, and EGCG) have been ingested internally for years without any reports of hair growth. The combination of these three compounds has the potential for a synergistic effect for hair loss prevention and/or hair growth promotion by interfering with the DHT receptor.

The invention is a topical formulation, utilizing caffeine, saw palmetto berry extract, and EGCG in combination, and provides a product for use in treatment of hair loss/balding that does not require a prescription for distribution or use.

Caffeine, saw palmetto berry extract, and EGCG are all known to have minimal side effects when used internally. Worldwide, caffeine is believed to be the most commonly ingested drug and tea is believed to be one of the most frequently ingested liquid beverages. Therefore, topical or local application of the invention is expected to be safe, as chronic oral exposure to these compounds is considered safe.

FORMULATIONS

Example 1

The first formulation, found in to U.S. Utility patent application Ser. No. 11/242,207, filed on Oct. 3, 2005, included two topical dihydroxytestosterone (DHT) blockers, caffeine and a saw palmetto berry extract. Approximately 2400 bottles were manufactured and sold with great patient satisfaction and return of patients to purchase more. Significant clinical improvement was observed by experienced dermatologists with this formulation.

The reduction of the previous caffeine concentration, an increase in saw palmetto extract concentration, and addition of epigallocatechin-3-gallate (EGCG) (a potent naturally-occurring DHT blocker) were contemplated to enhance the hair growth product.

Example 2

The updated formulation, found in U.S. Provisional Patent Application No. 61/441,063, filed on Feb. 9, 2011, included about 0.01 to 0.19 mg/ml of caffeine (about 0.001% to 0.019% weight of caffeine/final volume); about 0.01 to 0.2 mg/ml of saw palmetto berry extract (about 0.001% to 0.02% weight of saw palmetto berry extract/final volume); and about 75 to 150 mg/ml epigallocatechin-3-gallate (EGCG) (about 7.5% to 15% weight of EGCG/final volume).

EGCG in high concentration was found not to be feasible due to solubility problems. The separation of EGCG from the solution led to reductions in concentration.

Example 3

The current formulation, described herein, includes about 0.01 to 0.19 mg/ml of caffeine (about 0.001% to 0.019% weight of caffeine/final volume); about 0.01 to 0.2 mg/ml of saw palmetto berry extract (about 0.001% to 0.02% weight of saw palmetto berry extract/final volume); and about 0.5 to 50 mg/ml epigallocatechin-3-gallate (EGCG) (about 0.05% to 5% weight of EGCG/final volume).

The current formulation may affect local levels of androgenic hormones (i.e. testosterone and dihydroxytestosterone). Thus, it is recommended that this formulation be used only on men and women of non-childbearing potential considering that it has not been evaluated in women of childbearing ability.

Example 4

The current formulation is commercially available as a shampoo. This shampoo includes the following ingredients: D1 water, Sodium C14-16 Olefin Sulfonate, Cocamidopropyl Betaine, Cocamide DEA, Dimethiconol dodecylbenzensulfonate, TEA dodecylbenzensulfonate, Glycol Distearate, Sodium Chloride, Fragrance, Hydrolyzed Wheat Protein, Guar Hydroxypropyltrimonium Chloride, Epigallocatechin Gallate, Panthenol, Methylchloroisothiazolinone, Methylisothiazolinone, Caffeine, Serenoa Serrulata Fruit Extract, and Citric Acid.

Example 5

Clinical Case Studies

Over 1500 bottles of a commercial embodiment of the described composition (Pilaris Max® Shampoo) have been sold with continual multiple repeat orders. Positive results have been reported.

Study One: A 55-year old white male in the end stage of male-pattern hair loss (Hamilton IV) began using a commercial embodiment of the described composition (Pilaris Max® Shampoo) in July 2011. He used the shampoo every morning after swimming. He applied the shampoo to his moist scalp after swimming and leaves it on for a time period of fifteen minutes. Within a few weeks he noticed baby fine hairs appearing on his scalp. These baby fine hairs later converted to mature hairs over the next two months to the point where he required a haircut to the top of his head for the first time in years. He developed enough hair on the top of his head to the level that he began using hair color products. His co-workers and friends thought he had had a hair transplant.

Study Two: A 50-year old male began using a commercial embodiment of the described composition (Pilaris Max® Shampoo) in July 2011. He applied the shampoo to his scalp for the duration of his daily shower and any additional showers intermittently. He noticed a significant change from a photo taken in June 2011 before he began using the shampoo. In addition, a dermatologist he has known for sixteen years said "I have known you for years and you had significant thinning of the hair on top of your head, your hair is thicker now, so I know you have had hair transplants."

All patents and publications mentioned in this specification are indicative of the level of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The compositions, formulations, methods, techniques, systems, programs, and kits described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

What is claimed is:

1. A method for treating hair loss by reducing effects of 5α-dihydrotestosterone (DHT) in a subject undergoing treatment for hair loss, the method comprising:
    a) providing a composition consisting of
    about 0.01 to about 0.19 mg/ml of caffeine, which is about 0.001% to about 0.019% weight of caffeine/final volume;
    about 0.01 to about 0.2 mg/ml of a saw palmetto berry derivative, which is about 0.001% to about 0.02% weight of saw palmetto berry derivative/final volume;
    about 0.5 to about 50 mg/ml of an epigallocatechin-3-gallate (EGCG) derivative, which is about 0.05% to about 5% weight of EGCG/final volume;
    DI water; sodium C14-16 olefin sulfonate; cocamidopropyl betaine; cocamide ethanolamine; dimethiconol dodecylbenzensulfonate; TEA dodecylbenzensulfonate; glycol distearate; sodium chloride; fragrance; hydrolyzed wheat protein; guar hydroxypropyltrimonium chloride; panthenol; methylchloroisothiazolinone; methylisothiazolinone; and citric acid;
    b) moistening a scalp and hair of the subject undergoing treatment for hair loss;
    c) applying the composition to the scalp and hair moistened in step b;
    d) massaging the composition into the scalp and hair;
    e) leaving the composition on the scalp and hair for a period of time, whereby the composition penetrates the scalp to reduce effects of 5α-dihydrotestosterone (DHT) in the subject undergoing treatment for hair loss; and
    f) rinsing the composition from the scalp and hair.

2. The method according to claim 1, wherein the period of time is from about two to about five minutes.

3. A method for treating hair loss by reducing effects of 5α-dihydrotestosterone (DHT) in a subject undergoing treatment for hair loss, the method comprising:
    a) providing a composition consisting of
    about 0.01 to about 0.19 mg/ml of caffeine, which is about 0.001% to about 0.019% weight of caffeine/final volume;
    about 0.01 to about 0.2 mg/ml of a saw palmetto berry derivative, which is about 0.001% to about 0.02% weight of saw palmetto berry derivative/final volume;
    about 0.5 to about 50 mg/ml of an epigallocatechin-3-gallate (EGCG) derivative, which is about 0.05% to about 5% weight of EGCG/final volume;
    DI water; sodium C14-16 olefin sulfonate; cocamidopropyl betaine; cocamide ethanolamine; dimethiconol dodecylbenzensulfonate; TEA dodecylbenzensulfonate; glycol distearate; sodium chloride; fragrance; hydrolyzed wheat protein; guar hydroxypropyltrimonium chloride; panthenol; methylchloroisothiazolinone; methylisothiazolinone; and citric acid;
    b) moistening a scalp and hair of the subject undergoing treatment for hair loss;
    c) applying the composition to the scalp and hair moistened in step b;
    d) massaging the composition into the scalp and hair; and
    e) leaving the composition on the scalp and hair, whereby the composition penetrates the scalp to reduce effects of 5α-dihydrotestosterone (DHT) in the subject undergoing treatment for hair loss and the composition is not rinsed from the scalp or hair.

4. The method according to claim 3, wherein the composition is a leave-in conditioner.

5. The method according to claim 1, wherein the method is carried out daily, weekly, or in any time interval effective in providing desired improvements.

6. The method according to claim 3, wherein the method is carried out daily, weekly, or in any time interval effective in providing desired improvements.

* * * * *